United States Patent [19]

Mathew

[11] Patent Number: 5,023,382
[45] Date of Patent: Jun. 11, 1991

[54] SYNTHESIS OF 2,3-DISUBSTITUTED-2-CYCLOPENTENONES VIA LITHIOMETHYLMERCAPTO COMPOUNDS

[75] Inventor: Jacob Mathew, Fenton, Mo.

[73] Assignee: Petrolite Corporation, St. Louis, Mo.

[21] Appl. No.: 469,901

[22] Filed: Jan. 24, 1990

[51] Int. Cl.$^5$ ............................................. C07C 45/65
[52] U.S. Cl. .................................. 568/352; 568/312; 568/42; 549/78
[58] Field of Search .................. 508/42, 312, 352; 549/78

[56] References Cited

U.S. PATENT DOCUMENTS 4,073,799 2/1978 Kondo et al. ..................... 568/42

OTHER PUBLICATIONS

R. A. Ellison, Synthesis, 1973, 397.
M. Mikolajcayk, S. Grzejscak, & K. Korbacz, Tethedron Lett. 22, 3097 (1981).
M. Miklojczk, S. Grzejscak, & P. Kyzawa, Tetrahedron Lett., 23, 2237 (1982).
J. L. Herrmann, J. E. Richman, & R. H. Schlessinger, Tetrahedron Lett., 35, 3275 (1973).
P,. Bakuzis & M. L. F. Bakuzis, J. Org. Chem. 42, 2362 (1977).
S. C. Subramaniam, P. J. Thomas, V. R. Mamadapur, & M. S. Chadha, J., Chem. Soc. Perkin 1, 2346 (1979).
A. G. Cameron & A. T. Hewson, J. Chem. Soc. Perkin. Trans. 1, 2979 (1983).
I. Kawamoto, S. Muramatsu, & Y. Yura, Tetrahedron Lett. 48, 4223 (1974).
Y. Yura & J. Ide, Chem. Pharm. Bull, 17, 408 (1969).
J. L. E. Erickson & F. E. Collins, Jr., J. Org. Chem. 30, 1050 (1965).
K. Sisido, S. Torji, & M. Kawanisi, J. Org. Chem., 29, 904 (1964).
G. Buchi & B. Egger, J. Org. Chem., 36, 2022 (1971).
S. C. Welch, J. N. Assercq, J. P. Loh, & S. A. Glase, J. Org. Chem. 52, 1440 (1987).
P. Grieco, J. Org. Chem., vol. 37, No. 14, 2363 (1972).
T. Mukaiyama, J. Am. Chem. Soc., 94:24 (1972) pp. 8641-8642.

Primary Examiner—James H. Reamer
Attorney, Agent, or Firm—Jeffrey S. Boone

[57] ABSTRACT

2,3-disubstituted-2-cyclopenenones (such as cisjasmone) are prepared by (a) reacting an alkl 2-chloro-2,3-disubstituted-3-butenoate with a lithiomercaptan compound, (b) subjecting that product to reductive dehydrosulfurization. Methods of preparing the reactants are also disclosed.

15 Claims, No Drawings

SYNTHESIS OF 2,3-DISUBSTITUTED-2-CYCLOPENTENONES VIA LITHIOMETHYLMERCAPTO COMPOUNDS

BACKGROUND OF THE INVENTION

This invention relates to a new method for the synthesis of 2,3-disubstituted-2-cyclopentenone. In particular, the invention relates to such a method using lithium-sulfur compounds.

2,3-disubstituted-2-cyclopentenones are useful as fragrances and as pharmaceutical intermediates. For instance, 2-(cis-3-pentenyl)-3-methyl-2-cyclopentenone, commonly known as cis jasmone, and 2-pentyl-3-methyl-2-cyclopentenone, commonly known as dihydrojasmone, are expensive perfume ingredients, and 2,3-dimethyl-2-cyclopentenone is an intermediate useful in the synthesis of the antibiotic methylenomycin B.

2,3-disubstituted-2-cyclopentenones have been prepared by the intramolecular base catalyzed aldol-condensation of acyclic 1,4-dicarbonyl compounds (R. A. Ellison, Synthesis, 1973, 397; M. Mikolajcayk, S. Grzejsczak, and K. Korbacz, Tetrahedron Lett., 22, 3097 (1981); M. Miklojczyk, S. Grzejsczak, and P. Kyzawa, Tetrahedron Lett., 23, 2237 (1982); J. L. Herrman, J. E. Richmann, and R. H. Schlessinger, Tetrahedron Lett., 35, 3275 (1973); P. Bakuzis and M. L. F. Bakuzis, J. Org. chem. 42, 2362 (1977); S. C. Subramaniam, P. J. Thomas, V. R. Mamdapur, and M. S. Chadha, J. Chem. Soc. Perkin 1, 2346 (1979)), and by an intramolecular Wittig reaction effected by the treatment of the anion of α-diketones with vinyl triphenyl phosphonium salts (A.G. Cameron and A. T. Hewson, J. Chem. Soc. Perkin. Trans. 1, 2979 (1983); I. Kawamoto, S. Muramatsu, and Y. Yura, Tetrahedron Lett. 48, 4223 (1974)). Other routes based on dioxocyclopentanes (Y. Yura and J. Ide, Chem. Pharm. Bull, 17, 408 (1969)), cyclopentane-1,2-diones (J. L. E. Erickson and F. E. Collins, Jr., J. Org. Chem. 30, 1050 (1965)) and cyclodehydration of Y-lactones (K. Sisido, S. Torji, and M. Kawanisi, J. Org. Chem., 29, 904 (1964)), but these routes tend to be either very lengthy or involve the use of very expensive reagents. Other routes include (G. Buchi and B. Egger, J. Org. Chem., 26, 2021 (1971); S. C. Welch, J. N. Assercq, J. P. Loh, and S. A. Glase, J. Org. Chem., 52, 1440 (1987); P. Grieco, J. Org. Chem., Vol. 37, No. 14, (1972) p. 2363-2364; and T. Mukaiyama, J. Am. Chem. Soc., 94:24 (1972) p. 8641-8642).

SUMMARY OF THE INVENTION

Briefly, the invention comprises a novel method of preparing known 2,3-disubstituted 2-cyclopentenones by (a) reacting an alkyl 2-chloro, 2,3-disubstituted-3-butenoate with a lithiomercaptan compound, and (b) subjecting that product to reductive dehydrosulfurizaton.

The method of the invention is particularly easy and inexpensive to carry out and produces valuable products in good yield.

DETAILED DESCRIPTION OF THE INVENTION

In this specification and claims, numerical values are not critical unless otherwise stated. That is, the numerical values may be read as if they were prefaced with the words "about" or "substantially".

The invention is concerned with the synthesis of 2,3-disubstituted-2-cyclopentenones having the general formula:

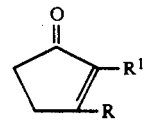

wherein $R^1$ is an organic moiety, generally an aryl, alkyl, or alkenyl, desirably a $C_1$ to $C_{32}$ alkyl or $C_2$ to $C_{32}$ alkenyl, more desirably a $C_1$ to $C_{12}$ alkyl or $C_2$ to $C_{12}$ alkenyl, preferably a $C_1$ to $C_8$ alkyl or $C_2$ to $C_8$ alkenyl, and most preferably a methyl, pentyl, or cis 2-pentenyl moiety; and R is an organic moiety, generally an aryl, alkyl, or alkenyl, desirably an alkyl, more desirably a $C_1$ to $C_{32}$ alkyl, preferably a $C_1$ to $C_{12}$ alkyl, more preferably a $C_1$ to $C_8$ alkyl, and most preferably a $C_1$ alkyl moiety. Preferred species include 2-(cis-2-pentenyl)-3-methyl-2-cyclopentenone (cis jasmone), 2-pentyl-3-methyl-2-cyclopentenone (dihydrojasmone), and 2,3-dimethyl-2-cyclopentenone.

One compound used in the process of the invention is an alkyl 2-chloro-2,3-disubstituted-3-butenoate. Such compounds have the general formula:

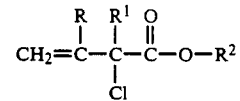

wherein R and $R^1$ are as defined above and $R^2$ is an alkyl, desirably a $C_1$ to $C_{12}$ alkyl, preferably a $C_1$ to $C_6$ alkyl, and most preferably a $C_2$ alkyl moiety. Alkyl 2-chloro-2,3-disubstituted-3-butenoates may be conveniently prepared by the reaction of an alkyl 2,3-disubstituted-2-butenoate of the formula:

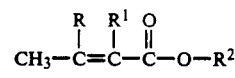

wherein R, $R^1$, and $R^2$ are as defined above, with Ca(OCl)$_2$ and ethanoic acid in a two phase system of water and dichloromethane, generally following the method of Wolinsky and coauthors in Tetrahedron Lett., 1981, 5019; and Tetrahedron Lett., 1980, 441; both of which are incorporated herein by reference.

Another method of preparing alkyl 2-chloro-2,3-disubstituted-3-butenoates is to react a 2-chloro-3-substituted-3-butenoate,

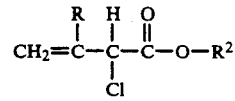

with a reactive compound such as an alkyl halide or an alkyl tosylate in the presence of a solvent such as tetrahydrofuran and a base such as potassium hexamethyldisilazide KN[Si(CH$_3$)$_3$]$_2$. In each case, the alkyl moiety replaced the hydrogen on the 2-carbon.

Another compound used in the process of the invention is a lithiomethylmercapto compound having a lithium-carbonsulfur-moiety. Examples of such compounds include 2-lithio-1,3-dithiane,

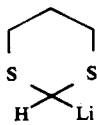

S-(lithiomethyl)mercaptobenzene,

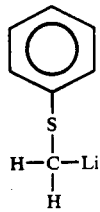

and bis(mercaptobenzene-S-)lithiomethane,

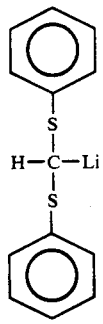

These compounds may be prepared by reacting the non-lithio counterpart with a 1-lithioalkane such as 1-lithiobutane and reduced temperature (e.g., −70° C.), and such preparation may take place in situ, in the reaction vessel for production of the cyclopentenone.

The alkyl 2-chloro-2,3-disubstituted-3-butenoate is preferably reacted with the lithiomethylmercapto compound in a solvent such as tetrahydrofuran, at −70° C. to ambient temperature, preferably at or below 0° C. This product is then subjected to reductive dehydrosulfurization, preferably with a catalyst such as Raney nickel, to yield the desired 2,3-disubstituted-2-cyclopentenone. Importantly, the structure of the 2,3-disubstituted-2-cyclopentenone is dependent only on the starting alkyl 2-chloro-2,3-disubstituted-3-butenoate and is totally independent of the structure of the lithiomethylmercapto compound because the reductive dehydrosulfurization removes all but a single carbon atom (and perhaps associated hydrocarbon atoms) of the lithiomethylmercapto compound. Thus, it can be seen that the only functions of the lithiomercaptothio compound are to donate a carbon atom and to close the ring structure. This is important because the synthesis of a specific 2,3-disubstituted-2-cyclopentenone is therefor dependent only on a single specific structural reagent (the alkyl 2-chloro-2,3-disubstituted-3-butenoate).

The final product may be purified by column chromatography. The final 2,3-disubstituted-2-cyclopentenone will be a single geometric isomer.

EXAMPLE 1

(Precursor, method i)

14 g (0.1 mole) of ethyl 2,3-dimethyl-2-butenoate was added in a single portion to a stirred suspension of 11 g (70 millimole) calcium hypochlorite in 20 ml of dichloromethane. The mixture was cooled to 0° C. and 50 ml of water was added, followed by rapid addition of 8 ml (0.14 mole) of glacial acetic acid. The cloudy, two-phase system was stirred in an ice bath for 15 minutes and then warmed to room temperature. 100 ml water and 200 ml dichloromethane were added, and the organic layer was isolated, washed with dilute sodium bicarbonate (2×40 ml), washed with water (40 ml), and then dried over anhydrous magnesium sulfate. Evaporation of solvents yielded 15 g of a colorless oil. Gas chromatography and gas chromatograph/mass spectroscopy indicated that the oil was 90% ethyl 2-chloro-2,3-dimethyl-3-butenoate, (Formula II, R=$CH_3$, $R^1$=$CH_3$).

EXAMPLE 2

(Precursor, method i)

Generally following the procedures of Example 1, the E-isomer of ethyl 2-methyl-3-phenyl-2-butenoate was used to produce ethyl 2-chloro-2-methyl-3-phenyl-3-butenoate Formula II, R=phenyl, $R^1$=methyl).

EXAMPLE 3

(Precursor, method ii)

Under nitrogen, 6 ml of hexamethyphosphoramide was added to a stirred solution of 4 g (20 millimole) potassium hexamethyldisilazide in 30 ml tetrahydrofuran. The mixture was cooled to −70° C. and a solution of 3.2 g (20 millimole) ethyl 2-chloro-3-methyl-3-butenoate in 5 ml tetrahydrofuran was added. The deep orange solution was stirred at −70° C. for 20 minutes and 1.2 equivalents of methyl iodide in 2 ml tetrahydrofuran was added rapidly. The mixture was stirred at −70° C. for another 15 minutes and then warmed to room temperature. The resulting yellow suspension was then quenched with 10 ml aqueous ammonium chloride and, after 15 minutes, diluted with 50 ml ether. The ether layer was washed with water (2×10 ml), 1N HCl (2×10 ml), 5% NaCl (10 ml), and dried over $MgSO_4$. Evaporation of the solvent yielded the crude product which was further purified by flash column chromatography prior to identification by $^1H$ NMR, $^{13}C$ NMR, and elemental analysis as ethyl 2-chloro-2,3-dimethyl-3-butenoate (Formula II, R =$CH_3$, $R^1$=$CH_3$).

EXAMPLE 4

(Precursor, method ii)

Generally following the procedure of Example 3, ethyl-2-chloro-3-methyl-3-butenoate was reacted with the following alkyl halides to produce the ester of Formula II in which R is $CH_3$ and $R^1$ is the alkyl moiety of the alkyl halide.
 a. $C_6H_5$—$CH_2$—Br;
 b. $CH_2$=CH—$CH_2$—Br;
 c.

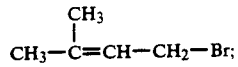

d. $CH_3-(CH_2)_4-I$;

e. $CH_3-CH_2-CH=CH-CH_2-Br$.

EXAMPLE 5

(Precursor, method ii)

Generally following the procedure of Example 3, ethyl 2-chloro-3-methyl-3-butenoate was reacted with 2-cispentenyl-1-tosylate

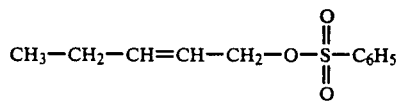

to produce ethyl 2-chloro-2-(2-cis-pentenyl)-3-methyl-3-butenoate.

EXAMPLE 6

(Invention)

Part A 1.2 ml (8 millimole) N,N,N',N'-tetramethyl-1,2-diaminoethane was added to a stirred solution of 1 g (8.2 millimole) thioanisole in 20 ml tetrahydrofuran, and the mixture was cooled to 0° C. while 3.4 ml (8 mole) of 2.5 M 1-lithiobutane was added dropwise. The cloudy mixture was warmed to room temperature and then, after 15 minutes, cooled to −70° C. and treated rapidly with a solution of 1.4 g (6.1 millimole) ethyl 2-chloro-2-(cis-2-pentenyl)-3-methyl-3-butenoate in 2 ml of tetrahydrofuran. The deep orange solution was slowly warmed to room temperature and it became deep brown. The solution was quenched with 10 ml of 1N NH4Cl. Extraction with ether (2×20 ml) and evaporation of solvent gave 1.5 g of a crude oil which was further purified by flash column chromatography on silica gel and identified as 2-(2-pentenyl)-3-methyl-5-phenylthio-2-cyclopenten-1-one

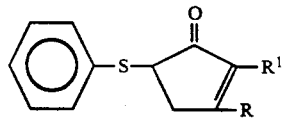

wherein $R^1$ is 2-pentenyl and R is methyl.

Part B

A solution of 0.8 g (2.95 millimole) of the product of Part A in 50 ml of acetone and 3 ml of Raney nickel was stirred at room temperature for 10–15 minutes. Thin layer chromatography was used to monitor the reductive dehydrosulfurization reaction. The mixture was filtered over celite and the colorless filtrate evaporated to give the crude product. Flash column chromatography on silica gel gave the product as a colorless oil. The structure was identified by IR, $^1$H NMR, $^{13}$C NMR, and mass spectrum as cis-jasmone.

EXAMPLES 7–11

(Invention)

Generally following the procedures of Example 6, similar compounds were made, the difference being the hydrocarbon substitution at the 2-position of the pentenone ring, corresponding to the hydrocarbon substitution at the 2-position of the precursor ester.

EXAMPLE 7

2-pentyl (product is dihydrojasmone)

EXAMPLE 8

2-(2-propenyl)

EXAMPLE 9

2-(3-methyl-2-butenyl)

EXAMPLE 10

2-benzyl

EXAMPLE 11

2-methyl.

EXAMPLE 12

(Invention)

Part A 4 ml (1 equivalent) of 2.5M 1-lithiobutane was added, with stirring, to a solution of 1.2 g (10 millimole) dithiane in 15 ml of tetrahydrofuran at −70° C. The pale yellow solution was stirred at this temperature for 45 minutes. A solution of 1.0 g (5.7 millimole) of ethyl 2-chloro-2,3-dimethyl-3-butenoate in 2 ml of tetrahydrofuran was added over a period of 30 seconds. The resulting solution was allowed to warm to room temperature over a period of 1 hour, gradually turning to a deep orange brown color. The solution was mixed with 20 ml ether and 5 ml NH4Cl. The organic extract was washed to yield a viscous yellow oil. The product was isolated by flash column chromatography to provide an intensely UV active solid having a pleasant odor (0.9 g, 74% yield), which was identified by IR, mass spectrum, $^{13}$C NMR, and $^1$H NMR as 2,3-dimethyl-2-cyclopentenone-5-spiro-2,6-dithiane.

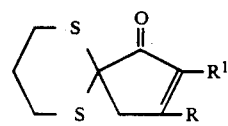

Part B

A solution of 0.84 g (4 millimole) of the product of Part A in 25 ml of ethanol was mixed with 1.2 ml of a slurry of Raney nickel and refluxed for 1 hour. The reaction mixture was cooled, filtered through celite, and the solvent evaporated to yield a colorless oil identified by IR, $^1$H NMR, $^{13}$C NMR and mass spectrum as 2,3-dimethyl-2-cyclopentenone, the same product as in Example 2.

What is claimed is:

1. A method of preparing a cyclopentenone compound of the formula:

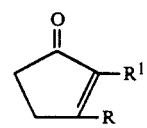

comprising a. reacting together i. an unsaturated ester of the formula:

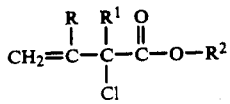

wherein R and R¹ are organic moieties and R² is an alkyl moiety; with ii. a mercaptan compound having a lithium-carbon-sulfur-moiety; and b. subjecting the product of step a. to reductive dehydrosulfurization.

2. The method of claim 1 wherein R and R¹ are each independently alkyl, alkenyl, or aryl.

3. The method of claim 2 wherein R is alkyl or alkenyl and R¹ as alkyl, alkenyl, or aryl.

4. The method of claim 3 wherein R is alkyl and R¹ is alkyl, alkenyl, or aryl.

5. The method of claim 2 wherein R and R¹ each independently have 1 to 32 carbon atoms.

6. The method of claim 4 wherein R and R¹ each independently have 1 to 8 carbon atoms.

7. The method of claim 4 wherein R is methyl.

8. The method of claim 7 wherein R¹ is methyl, pentyl, or cis-2-pentenyl.

9. The method of claim 1 wherein R² has 1 to 12 carbon atoms.

10. The method of claim 9 wherein R² has 1 to 6 carbon atoms.

11. The method of claim 10 wherein R² is ethyl.

12. The method of claim 1 wherein step a takes place at or below 0° C.

13. The method of claim 1 wherein the mercaptan compound having a lithium-carbon-sulfur moiety is formed in situ from the reaction of a mercaptan and a 1-lithioalkane.

14. The method of claim 1 wherein the reductive dehydrosulfurization takes place with the aid of a catalyst.

15. The method of claim 14 wherein the catalyst is Raney nickel.

* * * * *